United States Patent [19]

Eichinger et al.

[11] Patent Number: 5,585,521
[45] Date of Patent: Dec. 17, 1996

[54] PROCESS FOR THE PREPARATION OF ALKYLHYDRAZINE SALTS

[75] Inventors: Wolfram Eichinger, Köln; Helmut Fiege, Leverkusen, both of Germany

[73] Assignee: Bayer Aktiengesellschaft, Leverkusen, Germany

[21] Appl. No.: 532,909

[22] Filed: Sep. 22, 1995

[30] Foreign Application Priority Data

Sep. 29, 1994 [DE] Germany .......................... 44 34 847.9

[51] Int. Cl.$^6$ .................................................. C07C 241/02
[52] U.S. Cl. ............................................. 564/314; 564/310
[58] Field of Search ..................................... 564/310, 314

[56] References Cited

U.S. PATENT DOCUMENTS 4,954,655  9/1990  Kelly ........................................ 564/464

Primary Examiner—Richard L. Raymond
Attorney, Agent, or Firm—Sprung Horn Kramer & Woods

[57] ABSTRACT

Alkylhydrazine salts are prepared on an industrial scale and with good results by reacting together hydrazine, an alkene and a strong protonic acid in the presence of water, hydrazine and the protonic acid being introduced, the alkene being added, the liquid and gaseous phases present in the reaction vessel being intensively mixed together at 75° to 150° C., then the reaction mixture being cooled to temperatures below 60° C., the precipitated alkylhydrazine salt being separated off, hydrazine and strong protonic acid being again added to the mother liquor, then alkene being added again and the next reaction cycle being thus carried out.

11 Claims, No Drawings

PROCESS FOR THE PREPARATION OF ALKYLHYDRAZINE SALTS

The present invention relates to a process which can be carried out with good results on an industrial scale for the preparation of alkylhydrazine salts from hydrazine, a protonic acid and an alkene.

Alkylhydrazines are important intermediates for the preparation of medicaments and crop protection agents, e.g. for the preparation of N-t-alkyl-1,2-diacylhydrazines which have insecticidal activities.

JP-A2-63/72 661 (=Japanese application 61/218 729) discloses that alkylhydrazines can be prepared from hydrazine and an alkene in the presence of an inorganic acid. The reaction is only described on a small scale (0.1 mol of alkene) and the alkylhydrazine was not isolated but was only analysed in the reaction mixture. Not inconsiderable amounts of dialkylhydrazines are obtained as by-products.

According to U.S. Pat. No. 4,954,655, a very similar procedure is followed. Here also, the reaction is only described on a small scale (at most 0.16 mol of hydrazine). The alkylhydrazine prepared was not isolated here either, but a strong base and benzoyl chloride were added to the reaction mixture and finally N-t-alkyl-1,2-diacylhydrazines were obtained.

In both processes, the alkene is simply introduced into the reaction mixture or a great excess thereof is run through the reaction mixture.

In attempts to carry out these known processes on a larger scale, it was established that no further reaction then occurs, even if the reaction conditions are made more severe, e.g. the temperature and/or the pressure is increased, the reaction time is extended or the reaction mixture is stirred. Moreover, there is the requirement for a process in which the alkylhydrazines arise in pure form and can be isolated, because only then can the preparation of the alkylhydrazine and its further processing to medicaments and crop protection agents be carried out on separate sites (e.g. at different companies).

A process has now been found for the preparation of alkylhydrazine salts of the formula (I)

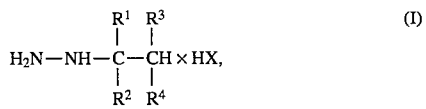

in which $R^1$ represents $C_1$–$C_4$-alkyl, $R^2$ represents $C_1$–$C_4$-alkyl, $C_2$–$C_4$-alkenyl, $C_2$–$C_4$-alkinyl or phenyl, $R^3$ and $R^4$, independently of each other, each represent hydrogen, $C_1$–$C_4$-alkyl, $C_2$–$C_4$-alkenyl or $C_2$–$C_4$-alkinyl or $R^1$ and $R^2$ or $R^3$ and $R^4$ together with the intermediate C atom represent $C_5$–$C_8$-cycloalkyl and X represents the anion of a strong protonic acid, from hydrazine and an alkene of the formula

in which $R^1$, $R^2$, $R^3$ and $R^4$ have the meaning specified under formula (I), in the presence of water and a strong protonic acid, which is characterized in that hydrazine and the protonic acid are introduced, the alkene of the formula (II) is added, the liquid and gaseous phases present in the reaction vessel are intensively mixed together at 75° to 150° C., then the reaction mixture is cooled to temperatures below 60° C., the precipitated alkylhydrazine salt of the formula (I) is separated off, hydrazine and strong protonic acid are again added to the mother liquor, then alkene of the formula (II) is again added and the next reaction cycle is thus carried out.

Alkenes of the formula (II) preferably to be used are, for example, isobutylene, 2-methyl-2-butene, 2-methyl-1-hexene, 2,3-dimethyl-butene, 1-methyl-cyclohexene, methylenecyclohexane and α-methylstyrene.

In the formulae (I) and (II), $R^1$ particularly preferably represents methyl or ethyl, $R^2$ particularly preferably represents methyl, ethyl, ethenyl or phenyl, in particular methyl or ethyl and $R^3$ and $R^4$, independently of each other, particularly preferably each represent hydrogen, methyl or ethyl, in particular both represent hydrogen.

Very particularly preferably, isobutylene is used in the process according to the invention and a mono-tert-butylhydrazine salt is prepared.

Strong protonic acids which can be used are, e.g., hydrogen fluoride, hydrogen chloride, hydrogen bromide, sulphuric acid, phosphoric acid and cationic ion-exchangers in the H form. Preference is given to hydrogen chloride and sulphuric acid. In formula (I), X therefore represents for example one equivalent of fluoride, chloride, bromide, sulphate, phosphate or ion-exchanger radical.

The strong protonic acids can be used as such or in the form of aqueous solutions. Mixtures of a plurality of strong protonic acids can also be used.

The water serves as solvent for the process according to the invention. It can be added in the form of hydrazine hydrate, aqueous protonic acids and/or as such.

The hydrazine can be used, e.g., as such, as hydrate, as hydrazinium salt of the protonic acid used and/or as an aqueous solution thereof.

It is advantageous to use the protonic acid in excess relative to hydrazine, for example 1.05 to 1.8 equivalents of protonic acid per mole of hydrazine.

The alkene can be used, e.g., in an amount of 0.5 to 1.5 mol per 1 mol of hydrazine. Preferably, this amount is 0.8 to 1.2 mol. The alkene can be used in liquid or gaseous form and can be added to the liquid and/or the gaseous phase.

Temperatures in the range from 85° to 110° C. are preferred for the reaction of hydrazine, protonic acid and alkene. The pressure in this reaction can be varied within broad ranges and can be, for example, 1 to 100 bar. A procedure under pressure or in a closed reaction vessel is generally advantageous in order to arrive at a good result.

It is an essential characteristic of the present invention that the liquid and gaseous phases present in the reaction vessel are intensively mixed together. Stirring with a simple stirrer is not sufficient for this.

The necessary intensive mixing can be achieved, e.g., by, e.g. beginning with the metering in of the alkene, continuously pumping off, in whole or in part, the liquid phase from the reaction vessel and atomizing it in the gas space of the reaction vessel. Likewise, the gaseous phase can be continuously pumped off, in whole or in part, from the reaction vessel and resupplied in finely divided form to the liquid phase. After addition of the alkene is completed, it is advantageous to continue the intensive mixing still for some time, e.g. 20 minutes to 4 hours or at least to stir the reaction mixture. In this manner, virtually quantitative conversion rates of the alkene used are achieved.

After this, the reaction mixture is cooled to temperatures below 60° C., preferably to −10° to +60° C., in particular to 0° to 20° C. During this between 20 and 40% by weight of the alkylhydrazine salt of the formula (I) present in the reaction mixture precipitates. It can be separated off, e.g., by filtration and if necessary washed with fresh water.

Although only a small proportion of the alkylhydrazine salt of the formula (I) formed is isolated in this manner, its preparation can nevertheless proceed in an economical manner, since it has surprisingly been shown that there is no undesirable enrichment of by-products if hydrazine and strong protonic acid are again added to the mother liquor after separating off the precipitated alkylhydrazine salt, then adding again alkene of the formula (II) and thus beginning the next reaction cycle. In total, the alkylhydrazine salt is then obtained in yields of approximately 90% of theory and inpurities of approximately 99%.

When the mother liquor, to :which the wash water can also be added if required, is reused, it is only necessary to take care that the reaction mixture does not become excessively dilute. This would occur, e.g., if the wash water is added to the mother liquor and/or the hydrazine is used in the form of hydrazine hydrate and/or the strong protonic acid is used as aqueous solution. An excessive dilution can be prevented, e.g., by distilling off water from the mother liquor and, if necessary, from the wash water.

Recycling the mother liquor can be repeated at least 20 times.

The reaction vessels for carrying out the process according to the invention must be resistant to strong protonic acids. They can be made of, e.g., glass, plastic, tantalum or tantalum alloys or can be coated with glass or enamel.

The process according to the invention permits the preparation and isolation of alkylhydrazine salts of the formula (I) on an industrial scale in good yields and with high purities.

EXAMPLES

Example 1

1630 g of 37% strength by weight aqueous hydrochloric acid, 701 g of hydrazine hydrate (=14 mol) and 470 g of water were introduced into a 4 l stirred autoclave made of steel/enamel. The reactor was closed and heated with stirring to 100° C. Then, in the course of 5.5 hours with vigorous stirring, 706 g of isobutylene were added in finely divided form beneath the liquid surface and at the same time the gas phase was partially pumped off via a gas pump and returned in finely divided form to the liquid phase. After the isobutylene addition was completed, the mixture was stirred for a further 1 hour. The reaction mixture was then cooled to +3° C., the precipitate which settled out was filtered off and the filter cake obtained was washed with 250 g of water. After the filter cake was dried, 471 g of tertbutylhydrazine hydrochloride were present in a purity of above 99%. This is equivalent to a yield of 28.2%, based on hydrazine.

Example 2 (for comparison)

Hydrochloric acid, hydrazine hydrate and water were introduced in accordance with Example 1. After the reaction vessel was closed, the reaction mixture was heated to 85° C. and 50 g of isobutylene were added to the gas space in the course of 20 minutes with stirring. During this, the pressure increased to 6 bar. Within the next 3 hours, no pressure decrease was observed. The temperature was then increased to 100° C. Again, in the course of 3 hours no pressure decrease was observed. Finally, the remaining 656 g of isobutylene were added (15.3 bar) and the reaction mixture was stirred for 18 hours at 100° C. Again no pressure decrease occurred. The reaction mixture was finally cooled to +3° C., no precipitates settling out. Obviously, no reaction had taken place.

Example 3

Example 1 was repeated, the mother liquor (3215 g) remaining after filtering off the reaction mixture was combined with the wash water and 500 g of water as distilled off from this mixture. The amounts of 37% strength by weight aqueous hydrochloric acid, hydrazine hydrate and isobutylene specified in the first line of Table 1 below were then added and reacted and worked up in accordance with Example 1. This reaction cycle was repeated 10 times. The details can be seen in Table 1 below.

TABLE 1

| Reaction cycle | Dosages (g) | | | | Product (g) separated off, dry |
| --- | --- | --- | --- | --- | --- |
| | Mother liquor | Hydrochloric acid | Hydrazine hydrate | Isobutylene | |
| 2 | 3215 | 400 | 193 | 236 | 510 |
| 3 | 3081 | 380 | 193 | 241 | 391 |
| 4 | 3147 | 400 | 193 | 236 | 604 |
| 5 | 2996 | 436 | 218 | 260 | 446 |
| 6 | 3162 | 370 | 187 | 232 | 540 |
| 7 | 3107 | 400 | 202 | 249 | 427 |
| 8 | 3251 | 390 | 181 | 201 | 549 |
| 9 | 3074 | 440 | 222 | 271 | 402 |
| 10 | 3252 | 356 | 180 | 213 | 533 |
| 11 | 2966 | 420 | 210 | 255 | 428 |

After a total of 11 reaction cycles, the overall yield of dry tert-butylhydrazine hydrochloride was 79.3% of theory, based on total hydrazine used. This yield becomes still higher if further reaction cycles are carried out.

What is claimed is:

1. A process for the preparation of alkylhydrazine salts of the formula

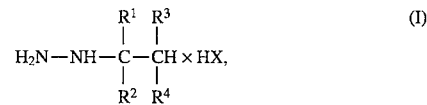

in which
R¹ represents $C_1$–$C_4$-alkyl,
R² represents $C_1$–$C_4$-alkyl, $C_2$–$C_4$-alkenyl, $C_2$–$C_4$-alkinyl or phenyl,
R³ and R⁴, independently of each other, each represent hydrogen, $C_1$–$C_4$-alkyl, $C_2$–$C_4$-alkenyl or $C_2$–$C_4$-alkinyl or
R¹ and R² or R³ and R⁴ together with the intermediate C atom represent $C_5$–$C_8$-cycloalkyl and
X represents the anion of a strong protonic acid,
from hydrazine and an alkene of the formula

in which
R¹, R², R³ and R⁴ have the meaning specified under formula (I),
in the presence of water and a strong protonic acid, in which process hydrazine and the protonic acid are introduced, the alkene of the formula (II) is added, the liquid and gaseous phases present in the reaction vessel are intensively mixed together at 75° to 150° C., then the reaction mixture is cooled to temperatures below 60° C., the precipitated alkylhydrazine salt of the formula (I) is separated off, hydrazine and strong protonic acid are again added to the mother liquor, then alkene of the formula (II) is again added and the next reaction cycle is thus carried out.

2. The process of claim 1, in which the alkene used is isobutylene, 2-methyl-2-butene, 2-methyl-1-hexene, 2,3-dimethyl-butene, 1-methyl-cyclohexene, methylenecyclohexane or α-methylstyrene.

3. The process of claim 1, in which in the formulae (I) and (II)

$R^1$ represents methyl or ethyl, $R^2$ represents methyl, ethyl, ethenyl or phenyl, $R^3$ and $R^4$, independently of each other, represent hydrogen, methyl or ethyl and X represents one equivalent of fluoride, chloride, bromide, sulphate, phosphate or an ion-exchanger radical.

4. The process of claim 1, in which the strong protonic acid used is hydrogen fluoride, hydrogen chloride, hydrogen bromide, sulphuric acid, phosphoric acid or a cationic ion exchanger in the H form.

5. The process of claim 1, in which 1.05 to 1.8 mol of protonic acid is used per mole of hydrazine.

6. The process of claim 1, in which the liquid phase is continuously pumped off in whole or in part from the reaction vessel and atomised in the gas space of the reaction vessel.

7. The process of claim 1, in which the gaseous phase is continuously pumped off in whole or in part from the reaction vessel and returned in finely divided form to the liquid phase.

8. The process of claim 1, in which the reaction mixture is cooled to 0° to 20° C.

9. The process of claim 1, in which some of the water present is distilled off from the mother liquor before its recycling.

10. The process of claim 1, in which reaction vessels are used which are made of glass, plastic, tantalum or tantalum alloys or are coated with glass or enamel.

11. A process for the preparation of alkylhydrazine salts of the formula

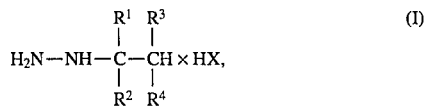  (I)

in which $R^1$ represents $C_1$–$C_4$-alkyl, $R^2$ represents $C_1$–$C_4$-alkyl, $C_2$–$C_4$-alkenyl, $C_2$–$C_4$-alkinyl or phenyl, $R^3$ and $R^4$, independently of each other, each represent hydrogen, $C_1$–$C_4$-alkyl, $C_2$–$C_4$-alkenyl or $C_2$–$C_4$-alkinyl or $R^1$ and $R^2$ or $R^3$ and $R^4$ together with the intermediate C atom represent $C_5$–$C_8$-cycloalkyl and X represents the anion of a strong protonic acid, which comprises reacting a hydrazine and an alkene of the formula

 (II)

in which $R^1$, $R^2$, $R^3$ and $R^4$ have the meaning specified under formula (I), in the presence of water and a strong protonic acid.

wherein said process comprises (1) introducing the hydrazine and the protonic acid into the autoclave;

(2) adding the alkene;

(3) intensively mixing the liquid and gaseous phases at a temperature of 75 ° C. to 150° C.;

(4) cooling the reaction mixture to a temperature below 60° C., (5) separating off the precipitate alkylhydrazine salt of the formula (I); and (6) adding hydrazine and the protonic acid to the mother liquor followed by the addition of the alkene and repeating the reaction cycle, wherein 1.05 to 1.8 mol of protonic acid and 0.5 to 1.5 mol of alkene per mole of hydrazine are used and the reaction vessel in the autoclave is made of glass, plastic, tantalum, tantalum alloys, or steel coated with glass or enamel.

* * * * *

UNITED STATES PATENT AND TRADEMARK OFFICE
CERTIFICATE OF CORRECTION

PATENT NO. : 5,585,521
DATED : December 17, 1996
INVENTOR(S) : Eichinger, et al.

It is certified that error appears in the above-indentified patent and that said Letters Patent is hereby corrected as shown below:

Title Page     Under [56] References Cited: Insert -- OTHER PUBLICATIONS: Dewent abstract of JP 63-072,661, (4/2/88). --

Col. 6, line 46     Delete " ofalkene " and substitute -- of alkene --

Signed and Sealed this

Third Day of June, 1997

Attest:

BRUCE LEHMAN

Attesting Officer     Commissioner of Patents and Trademarks